United States Patent [19]

Nash-Morgan

[11] Patent Number: 5,582,585
[45] Date of Patent: Dec. 10, 1996

[54] DISPOSABLE ELASTIC NECK AND FACIAL WRINKLE GATHERING DEVICE

[76] Inventor: Leonora E. Nash-Morgan, 3524 E. Forest Lake Dr., Sarasota, Fla. 34232

[21] Appl. No.: 533,008

[22] Filed: Sep. 25, 1995

[51] Int. Cl.$^6$ ................................ A61F 13/12
[52] U.S. Cl. .................. 602/44; 428/230; 428/231; 428/232; 428/343; 602/74; 606/204.35
[58] Field of Search ............. 606/204.35, 213–216; 602/41–59; 428/235, 261, 343, 230, 231, 232

[56] References Cited

U.S. PATENT DOCUMENTS

| | | | |
|---|---|---|---|
| 363,538 | 5/1887 | Penny | 606/213 |
| 1,023,358 | 4/1912 | Bender | 604/303 |
| 1,996,703 | 4/1935 | Giuliano | 604/303 |
| 3,709,225 | 1/1973 | Sobel | 604/303 |
| 4,366,814 | 1/1983 | Riedel | 428/230 X |
| 4,658,811 | 4/1987 | Beaird | 602/77 |
| 4,734,320 | 3/1988 | Leonardi | 428/231 |
| 5,116,675 | 5/1992 | Nash-Morgan | 428/343 |

Primary Examiner—Stephen R. Crow
Assistant Examiner—Kim M. Lee
Attorney, Agent, or Firm—Charles J. Prescott

[57] ABSTRACT

A disposable adhesively engagable neck and facial wrinkle gathering device which in one embodiment includes an elongated fully elastic main strip formed of flexible nonwoven hypoallergenic elastic tape adhesively coated on one entire side thereof. This embodiment also includes a non-adhesive fully elastic fabric central strip adhered against and coextensive with a central length of the adhesive side of the main strip. Another embodiment includes a length of slender elastic string connectable at each end thereof to an elastic or non-elastic adhesive strip having one adhesive surface. Both embodiments are structured to extend either partially around to the sides and back of the user's neck from the nape of the neck or downwardly from around the top of the base of the ear along either side of the ear or from the sides of the face around the back or over the crown of the head. When so positioned, with the central elastic portion stretched, the facial or neck skin is drawn back away from the face to stretch and flatten wrinkles and flabby tissue.

1 Claim, 3 Drawing Sheets

U.S. Patent     Dec. 10, 1996     Sheet 1 of 3     5,582,585
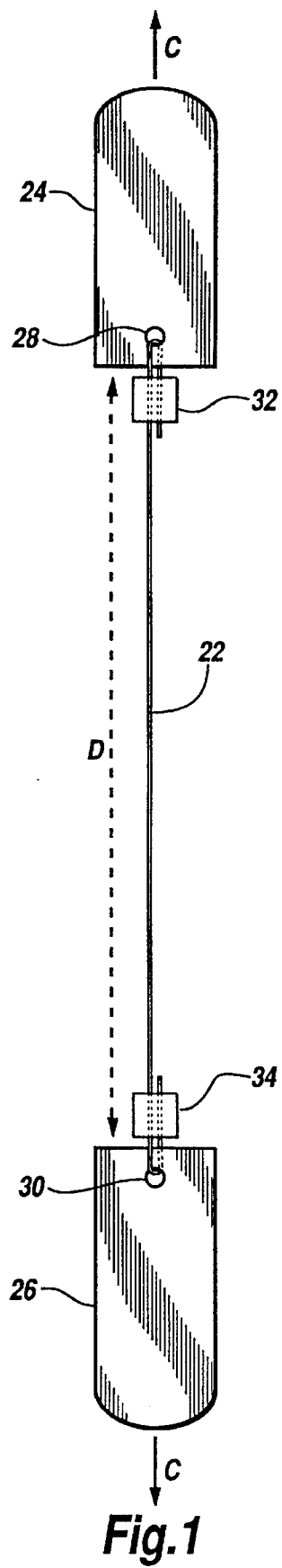
Fig.1
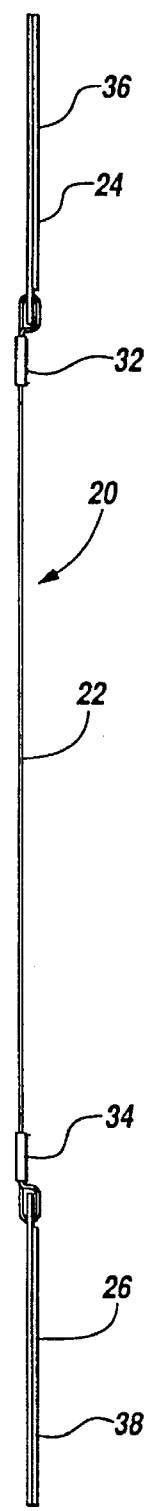
Fig.2
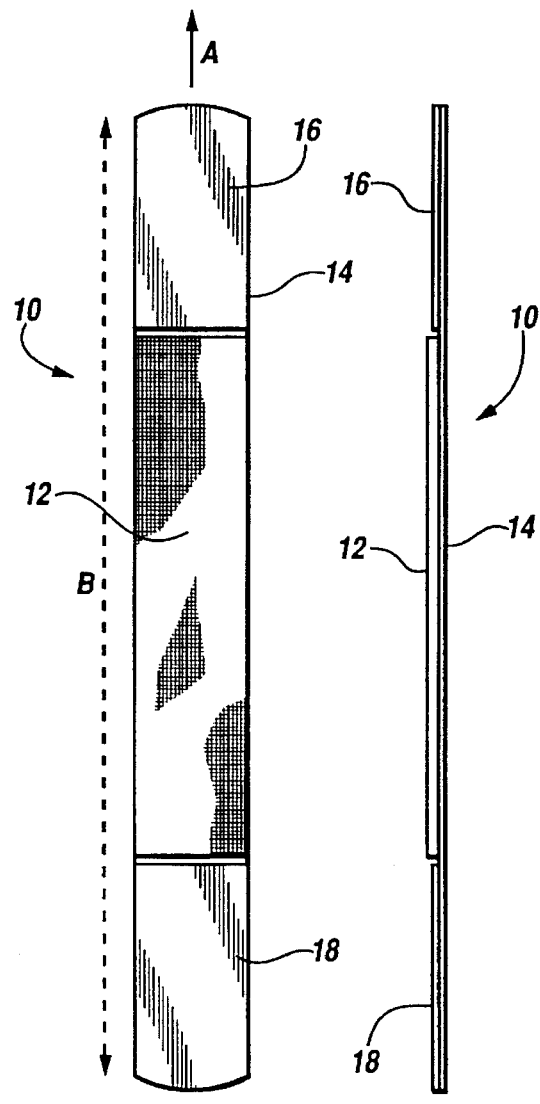
Fig.3
Fig.4

DISPOSABLE ELASTIC NECK AND FACIAL WRINKLE GATHERING DEVICE

BACKGROUND OF THE INVENTION

SCOPE OF INVENTION

This invention relates generally to elasticized adhesive strips, and more particularly to a disposable elasticized neck and facial wrinkle gathering device which is adhesively connected to the sides of the face and neck.

PRIOR ART

As men and women age, the neck and facial muscles and skin tissue generally lose muscle tone and become wrinkled and flaccid. The appearance of wrinkles in the lower face, neck, lower jaw area and the temple area behind the eyes are some of the more prominent facial features which exhibit this aging characteristic.

To alleviate this problem for those unable to deal with this aging process, cosmetic surgery or a "face lift" to remove excess skin tissue has provided one rather expensive alternative to maintaining a more youthful appearance.

Modern chemical topically applied cosmetic products are also available which tend to moisten and/or cause the skin to temporarily contract or shrink to reduce the unsightly facial, chin, neck and eye (crow's foot) wrinkles. Additionally, heavier applications of conventional makeup also serve to disguise these aging effects.

My previous U.S. Pat. No. 5,116,675 teaches a device similar to that of the present invention directed to a disposable adhesive neck and facial wrinkle gathering device which includes a central elastic portion and opposingly extending non-elastic adhesive strips connected at each end thereof to the elastic portion. However, because of the nonexpandable nature of the adhesive strips, the degree of stretchability of this device is somewhat limited and tends to be more uncomfortable to wear during long periods of use.

The present invention provides a more comfortable and conveniently useable, disposable alternative to the presently available techniques and prior art devices for retarding the appearance of aging. This invention, to that end, provides a fully elasticized adhesive neck and facial wrinkle gathering device in one embodiment which is intended to be worn comfortably on a temporary basis which will stretch and draw wrinkled skin away from the more visible areas of the neck, jaw and face rearwardly and upwardly so as to smooth the broader areas of wrinkled skin in these areas. Another embodiment of the invention provides a central elastic string connected at each end thereof to elastic or non-elastic "skin tape" which adhesively attaches to these areas of the face and neck adjacent to the wrinkled areas. The elastic string, when fully stretched, becomes very unobtrusive when covered with hair over the head or at the back of the head and lower neck of the user.

Although not a permanent or long-lasting remedy for facial wrinkles, nonetheless both embodiments of the present invention are easily applied by the user prior to public appearances and provides the psychological benefit of a "facelift" during those brief time periods.

BRIEF SUMMARY OF THE INVENTION

This invention is directed to a disposable adhesively engagable neck and facial wrinkle gathering device which in one embodiment includes an elongated fully elastic main strip formed of flexible non-woven elastic tape adhesively coated on one entire side thereof. This embodiment also includes a non-adhesive fully elastic fabric central strip adhered against and coextensive with a central length of the adhesive side of the main strip. Another embodiment includes a length of slender elastic string connectable at each end thereof to an elastic or a non-elastic adhesive strip having one adhesive surface. Both embodiments are structured to extend either partially around to the sides and back of the user's neck from the nape of the neck or downwardly from around the top of the base of the ear along either side of the ear or from the sides of the face around the back or crown of the head. When so positioned, with the central elastic portion stretched, the facial or neck skin is drawn back away from the face to stretch and flatten wrinkles and flabby tissue.

It is therefore an object of this invention to provide the disposable elasticized adhesive neck and facial wrinkle gathering device which is easily applied by the user and comfortably worn for the temporary smoothing and stretching of prominent skin areas of the face, neck and jaw.

It is yet another object of this invention to provide a disposable fully elasticized neck and facial wrinkle gathering device which is an economical and easily applied alternative to "facelifts" for achieving a temporary more youthful facial appearance.

It is yet another object of this invention to provide a disposable and unobtrusive means for temporarily removing wrinkles from neck and facial skin by stretching those areas toward a less prominent area behind the neck and head areas of the user.

In accordance with these and other objects which will become apparent hereinafter, the instant invention will now be described with reference to the accompanying drawings.

BRIEF DESCRIPTION OF THE DRAWINGS

FIG. 1 is a front elevation view of one embodiment of the invention.

FIG. 2 is a side elevation view of FIG. 1.

FIG. 3 is a front elevation view of another embodiment of the invention.

FIG. 4 is a side elevation view of FIG. 3.

DETAILED DESCRIPTION OF THE INVENTION

Figure 5:
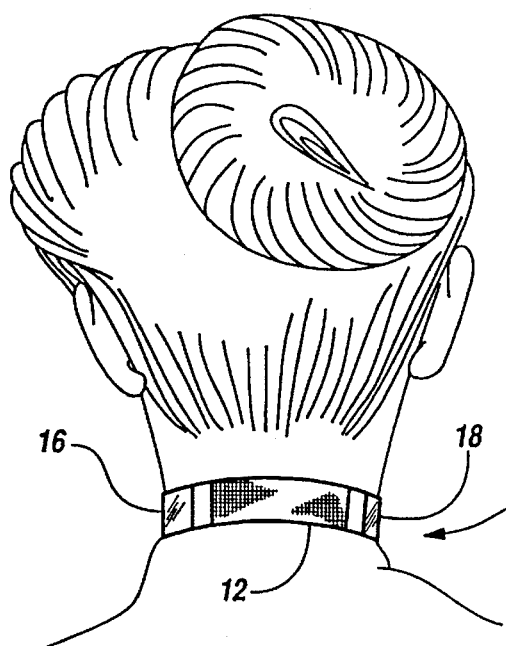
FIG. 5 is a rear perspective view of the invention shown in FIG. 1 in use attached around the nape and sides of the user's neck.

Referring now to the drawings, and particularly to FIGS. 3 and 4, one embodiment of the invention is shown generally at numeral 10. This embodiment 10 includes a central, longitudinally elongated fully elastic main strip 14 formed of non-woven adhesive elastic tape as manufactured by the 3M Company under their product No. 9906T. This material is fully elastic, stretching to between six and seven times its free length in either longitudinal or transverse directions. In one embodiment, the 3M tape is provided with a hypoallergenic adhesive on one side thereof as utilized by the present invention.

A central strip 12 formed of non-adhesive fully elastic flexible fabric material is sized permanently adhered to the central portion of the main strip 14. Permanent adhesion between the two members 12 and 14 is accomplished by the adhesive preapplied onto one surface of the main strip 14 as above described. The preferred material utilized to form the central strip 12 is manufactured by Darlington Industries under their trade number 2241 and thus provides a non-adhesive fully extensible central surface of the device which disposes a comfortable non-adhesive surface against the majority of the skin area which this embodiment 10 encounters in use.

To protect the adhesive surfaces of main strip 14 prior to use, a removable cover sheet known as liner 16 and 18 formed of thin non-elastic and non-porous material is attached thereto. Removal of these cover sheets 16 and 18 is accomplished in the wellknown manner simply by pealing them away immediately prior to use of the device 10.

After removal of the protective cover sheets 16 and 18, the device 10 is thus stretchable or expandable by pulling in the direction of arrows A so that virtually the entire length of the device 10 expands uniformly in the direction of arrow B, the multi-layer central portion defined by central strip 12 also expands elastically in a uniform manner to at least twice the length of the device 10 in its free, relaxed configuration.

Referring now to FIGS. 1 and 2, another embodiment of the invention is shown generally at numeral 20 and includes an elongated length of slender elastic string 22 having an elongated elastic or non-elastic adhesive strip 24 and 26 of a hypoallergenic, generally transparent or translucent material connected thereto. Connection between each end of the elastic string 22 and elastic strips 24 and 26 is accomplished by passing each end of the string 22 through holes 28 and 30 and doubled back on itself to be secured by conventional light-weight fasteners 32 and 34. In this embodiment 20, the elasticity of the device is provided only by the elastic string 22 stretching in the direction of arrow D when each elastic strip 24 and 26 is pulled in the direction of arrow C.

This embodiment 20 also includes protective cover sheets 36 and 38 which protect the adhesive surface therebelow until the device 20 is ready for use.

Figure 6:
FIG. 6 is a front perspective view of FIG. 5.

Referring now to FIGS. 5 and 6, the embodiment 10 previously described in FIGS. 3 and 4 is there shown in use. The central elastic strip 12 and fully interconnected central portion of main strip 14 have been stretched or elongated manually near to or at its maximum level of extensibility after removing the cover sheets 16 and 18. Thereafter, the exposed adhesive surfaces of the end portions of the main strip 14 are applied against the sides of the neck and adhered in place manually by pressure with central strip 12 against the skin. By this arrangement, the resilient tension exerted by the stretched elastic main strip 14 and central strip 12 acting in the front and sides of the neck rearwardly in the direction of arrows E and F having the effect of flattening and smoothing the wrinkled areas in this facial and neck region.

Figure 7:
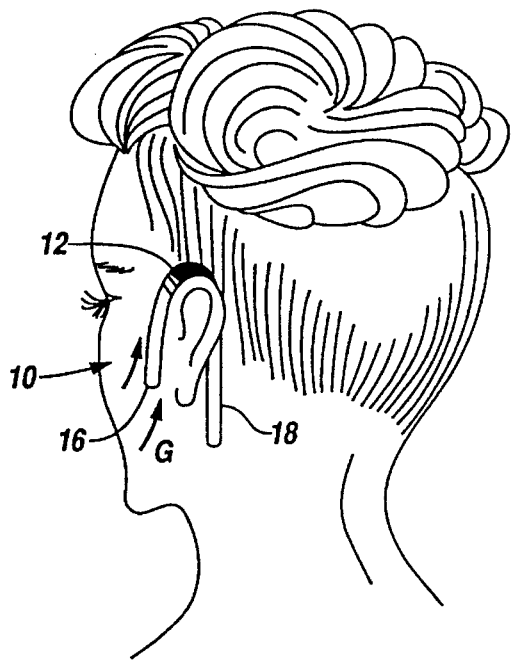
FIG. 7 is a rear perspective view of another use of the invention as shown in FIG. 3.

In FIG. 7, the embodiment of the invention 10 in a narrow width will comfortably fit around the top of the base of the ear so that the exposed end adhesive surfaces of the main strip 14, when cover sheets 16 and 18 are removed, will adhere alongside of the front and rear of the ear as shown. Stretching prior to adhesive connection will thus draw the skin in the jaw and upper neck area upwardly in the direction of arrow G resulting in the diminishing of the appearance of skin wrinkles, temporarily increasing firmness of the skin in these facial areas.

It is emphasized that the present invention in both embodiments is intended to be a disposable and temporarily used device and is not intended to be left adhered in place for long periods of time. There are no residual benefits claimed or anticipated after removal of the invention.

Figure 8:
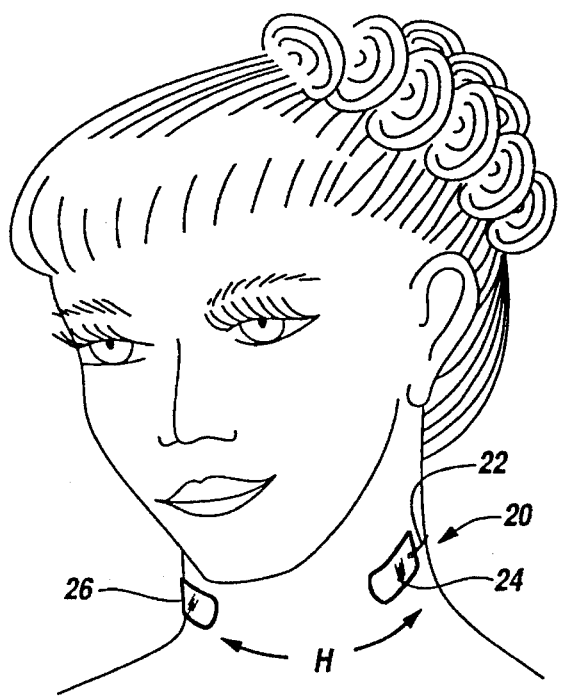
FIG. 8 is a front perspective view of the embodiment of the invention shown in FIG. 1 in use.
Figure 9:
FIG. 9 is a rear perspective view of FIG. 8.

Referring now to FIGS. 8 and 9, the embodiment 20 of the invention previously described in FIGS. 1 and 2 is there shown in use. Installation and useful effectiveness are similar to that described in FIGS. 5 and 6. The elastic or non-elastic adhesive strips 24 and 26 are manually adhered to the sides of the neck as shown after the elastic string 22 has been stretched to near its maximum length. Referring back to FIGS. 1 and 2, the connectors 32 and 34 may be easily adjusted to vary the overall relaxed length of the elastic string 22 so as to accommodate various sizes and needs of each user. By the elasticity of elastic string 22 in the direction of arrow J, the wrinkled skin the front and sides of the neck is drawn rearwardly in the direction of arrows H in FIG. 8 to both flatten and smooth these wrinkled areas of the face and neck.

Figure 10:
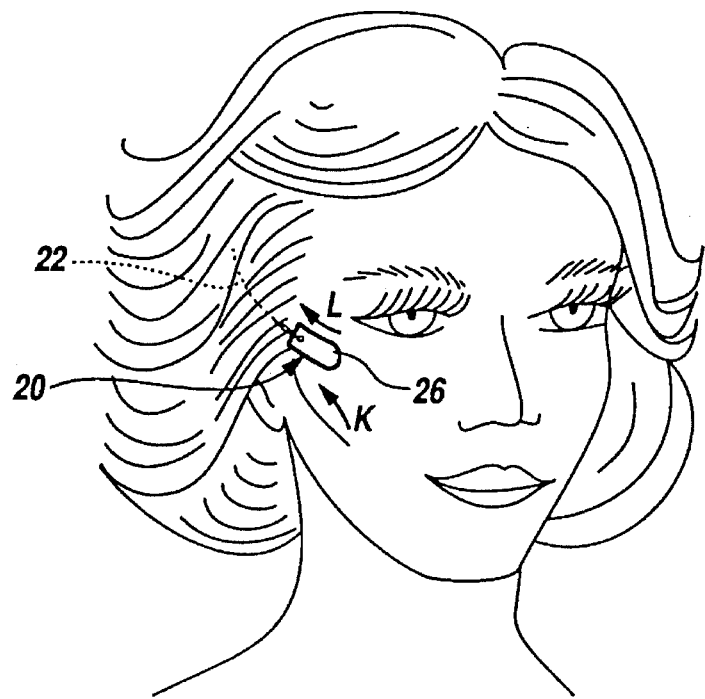
FIG. 10 is a front perspective view of the invention shown in FIG. 1 in use attached behind and below the eyes of the user partially concealed in the hair behind the head of the user.

Referring lastly to FIG. 10, an alternate use of the embodiment 20 is there shown. Each non-elastic adhesive strip 24 (not shown) and 26 are adhered adjacent and rearwardly of the eyes where there are "crows feet" after elastic expansion of the elastic string 22. The wrinkled "crows feet" area and cheek skin are drawn in the direction of arrows L and K, respectively rearwardly, the elastic string 22 being concealed within hair at the convenience of the user.

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

What is claimed is:

1. A disposable neck and facial wrinkle gathering device structured for unobtrusive appearance when worn cosmetically comprising:

an elongated length of slender elastic string;

an elongated adhesive strip having a one adhesive surface and structure at one end thereof for adjustable connection to each end of said elastic string a whereby a distance along a relaxed length of said elastic string between each said adhesive strip is selectively variable;

said relaxed length of said elastic string is at least twice a length of each said adhesive strip;

said elastic string sized in length and elasticity to be stretched in length to partially encircle the back of a user's neck or head to allow each said adhesive strip, after being connected to each end of said elastic string, to be adhered to opposing sides of the neck or face of the user;

said stretched elastic string elastically acting through and being supported by said connected adhesive strips adhered to the opposing sides of the neck or face, to draw skin on the anterior of the neck or sides of the face rearwardly or upwardly whereby wrinkles in the neck anterior skin or sides of the face are stretched and generally flattened.

* * * * *